US006939691B1

(12) United States Patent
Khosla et al.

(10) Patent No.: US 6,939,691 B1
(45) Date of Patent: Sep. 6, 2005

(54) E. COLI AND STREPTOMYCES HOST CELLS THAT CONTAIN MATBC GENES OR E. COLI HOST CELLS THAT CONTAIN PCC GENES USEFUL FOR ENHANCED POLYKETIDE PRODUCTION

(75) Inventors: Chaitan Khosla, Palo Alto, CA (US); Blaine Pfeifer, Palo Alto, CA (US)

(73) Assignee: Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/687,855

(22) Filed: Oct. 13, 2000

Related U.S. Application Data

(60) Provisional application No. 60/232,379, filed on Sep. 14, 2000, provisional application No. 60/206,082, filed on May 18, 2000, provisional application No. 60/159,090, filed on Oct. 13, 1999.

(51) Int. Cl.$^7$ ............................................. C12P 19/62
(52) U.S. Cl. ............... 435/76; 435/252.35; 435/252.33
(58) Field of Search ..................... 435/252.3, 252.33, 435/252.35, 252.31

(56) References Cited

U.S. PATENT DOCUMENTS

| | | | |
|---|---|---|---|
| 5,672,491 A | | 9/1997 | Khosla et al. ............... 435/148 |
| 5,830,750 A | * | 11/1998 | Khosla et al. ......... 435/252.35 |
| 6,033,883 A | | 3/2000 | Barr et al. ................... 435/148 |
| 6,258,566 B1 | * | 7/2001 | Barr et al. ..................... 435/76 |
| 6,579,695 B1 | * | 6/2003 | Lambalot et al. ............. 435/41 |
| 2002/0142401 A1 | * | 10/2002 | Santi et al. .................... 435/76 |

FOREIGN PATENT DOCUMENTS

| | | |
|---|---|---|
| WO | WO 9508548 | 3/1995 |
| WO | WO 9827203 | 6/1998 |
| WO | WO 9903986 | 1/1999 |
| WO | WO 9919518 | 4/1999 |
| WO | WO 0020601 | 4/2000 |

OTHER PUBLICATIONS

An et al. A gene cluster encoding malonyl-CoA decarboxylase (MatA), malonyl-CoA synthetase (MatB) and a putative dicarboxylate carrier protein (MatC) in Rhizobium trifolii. Eur. J. Biochem. (1998) 257:395-402.*

Spratt et al. Isolation and genetic characterization of Escherichia coli mutants defective in propionate metabolism. J Bacteriol (1981) 146(3):1166-9.*

Donadio, S. et al. (1996). *Molecular Microbiology* 19(5): 977-984.
Gokhale, R.S et al. (1999). *Science* 284:482-485.
Hsieh, Y-J et al. (1994). *Journal of Bacteriology* 176(3): 714-724.
Kao, C.M. et al. (1994). *Science* 265(5171):509-512.
Khosla, C. et al. (1999). *Annual Review of Biochemistry* 68:219-253.
Pfeifer, B.A. et al. (2001). *Microbiology and Molecular Biology Reviews* 65(1):106-118.
Pfeifer, B.A. et al. (2001). *Science* 291(5509):1790-1792.
Quadri, L.E. et al. (1998). *Biochemistry* 37(6):1585-1595.
Rodriquez, E. et al. (1999). *Microbiology* 145:3109-3119.
Stassi, D.L. et al. (1998). *Proceedings of the National Academy of Sciences of USA* 95(13):7305-7309.
Tang, L. et al. (1994). *Journal of Bacteriology* 176(19): 6107-6119.
Umeyama, T. et al. (1996). *FEMS Microbiology Letters* 144(2-3):177-184.
Zhang, W. et al. (1999). *Applied Biochemistry and Biotechnology* 82(3):209-225.
Ziermann, R. et al. (1999). *Biotechniques* 26(1):106-110.
Floss, et al. (1999) *Current Opinion in Chemical Biology* 3:592-597.
Hunziker, et al. (1998) *J Am Chem Soc* 120:1092-1093.
Schupp, et al. (1998) *FEMS Microbiology Letters* 159:201-207.

\* cited by examiner

*Primary Examiner*—Kathleen Kerr
(74) *Attorney, Agent, or Firm*—Morrison & Foerster LLP

(57) ABSTRACT

The use of enzymes that catalyze the production of starter and extender units for polyketides in *E. coli* and *Streptomyces* is described; these enzymes include malonyl CoA decarboxylase (MatA), malonyl CoA synthetase (MatB), and a malonate transporter (MatC) as well as proprionyl CoA carboxylase (pcc). The matBC gene from *Streptomyces coelicolor*, the matABC genes from *Rhizobium trifoli*, and the pccB and accA2 from *Streptomyces coelicolor* are useful in specific embodiments of the claimed invention. These enzymes may be used to enhance the yield of polyketides that are natively produced or polyketides that are rationally designed. By using these techniques, the synthesis of a complete polyketide has been achieved in *E. coli* in the presence of a phosphopantetheinyl transferase, such as sfp from *Bacillus subtilis*. This achievement permits a host organism with desirable characteristics to be used in the production of such polyketides and to assess the results of gene shuffling.

27 Claims, No Drawings

E. COLI AND STREPTOMYCES HOST CELLS THAT CONTAIN MATBC GENES OR E. COLI HOST CELLS THAT CONTAIN PCC GENES USEFUL FOR ENHANCED POLYKETIDE PRODUCTION

CROSS-REFERENCE TO RELATED APPLICATIONS

This application claims priority under 35 U.S.C. § 119(e) to application Ser. No. 60/159,090 filed 13 Oct. 1999; Ser. No. 60/206,082 filed 18 May 2000; and Ser. No. 60/232,379 filed 14 Sep. 2000, which are expressly incorporated herein by reference.

STATEMENT OF RIGHTS TO INVENTIONS MADE UNDER FEDERALLY SPONSORED RESEARCH

This invention was made with U.S. government support from the National Institutes of Health and the National Science Foundation. The U.S. government may have certain rights in this invention.

TECHNICAL FIELD

The invention relates to methods to adapt procaryotic hosts for efficient production of polyketides. In one aspect, the hosts are modified to synthesize the starter and/or extender units used by polyketide synthases in the synthesis of polyketides. Other host modifications may also be made. Thus, the invention includes methods for production of complex polyketides in such diverse organisms as *Escherichia coli*, *Bacillus*, *Myxococcus*, and *Streptomyces*.

BACKGROUND ART

Complex polyketides such as 6-deoxyerythronolide B (6-dEB), the macrocyclic core of the antibiotic erythromycin, constitute an important class of natural products. They are synthesized by "modular" polyketide synthases, generally found in actinomycetes. For example, the polyketide synthase (PKS) which results in the synthesis of 6-dEB is produced in *Sacromyces erythraea*. The polyketides produced in these native hosts are generally subsequently tailored to obtain the finished antibiotic by glycosylation, oxidation, hydroxylation and other modifying reactions. Recent work from this laboratory has demonstrated that it is possible to express polyketide synthase modules in a functional form in *Escherichia coli* (Gokhale, R. S., et al., *Science* (1999) 284:482–485). However, in order to harness these modular enzymes for polyketide biosynthesis in *E. coli*, or in other hosts that do not normally produce them it is also necessary to produce their appropriate substrates in vivo in a controlled manner. For example, metabolites such as acetyl-CoA, propionyl-CoA, malonyl-CoA and methylmalonyl-CoA are the most common substrates of these enzymes. *E. coli* has the capability to produce acetyl-CoA, propionyl-CoA, and malonyl-CoA; however, the latter two substrates are only present in small quantities in the cell, and their biosynthesis is tightly controlled. The ability of *E. coli* to synthesize methylmalonyl-CoA has not been documented thus far.

Similar conditions prevail in other microbial cells, especially those that do not natively produce polyketides, such as various species of *Escherichia, Bacillus, Pseudomonas,* and *Flavobacterium*. Thus, generally, the required starter and/or extender units may not be produced in adequate amounts in any particular host. Further, by appropriate selection of the acyl transferase (AT) domains of the PKS in question, substrates more complex than those just mentioned may be employed. As an example, the PKS for synthesis of FK506 comprises an acyl transferase domain that incorporates substrates such as propyl malonyl-CoA in preference to malonyl-CoA or methylmalonyl-CoA. It would be helpful to have available a method which provides this range of substrates in appropriate levels in any arbitrarily chosen host organism.

Additional problems that may need to be surmounted in effecting the production of polyketides in procaryotic hosts, especially those which do not natively produce polyketides, include the presence of enzymes which catabolize the required starter and/or extender units, such as the enzymes encoded by the prp operon of *E. coli*, which are responsible for catabolism of exogenous propionate as a carbon and energy source in this organism. In order to optimize production of a polyketide which utilizes propionyl CoA as a starter unit and/or utilizes its carboxylation product, methylmalonyl CoA as an extender unit, this operon should be disabled, except for that portion (the E locus) which encodes a propionyl CoA synthetase. Any additional loci which encode catabolizing enzymes for starter or extender units are also advantageously disabled.

In addition, a particular procaryotic host, such as *E. coli*, may lack the phosphopantetheinyl transferase required for activation of the polyketide synthase. It may be required to modify the host to contain such a transferase as well.

In summary, it would be advantageous to effect the production of polyketides in microbial, especially procaryotic hosts in general, and, in particular, in hosts which do not natively produce polyketides. These hosts often have advantages over native polyketide producers such as *Streptomyces* in terms of ease of transformation, ability to grow rapidly in culture, and the like. These advantages are particularly useful in assessing the results of random mutagenesis or gene shuffling of polyketide synthases. Thus, the invention provides a multiplicity of approaches to adapt microbial hosts for the production of polyketides.

DISCLOSURE OF THE INVENTION

The invention has achieved, for the first time, the production of a complete polyketide product, 6-dEB, in the ubiquitously useful host organism, *E. coli*. The methods used to achieve this result are adaptable to microbial hosts in general, especially procaryotes. They can be used to adapt microbial hosts which do not natively produce polyketides to such production and to enhance the production of polyketides in hosts that normally produce them. Depending on the host chosen, the modifications required may include incorporation into the organism of expression systems for the polyketide synthase genes themselves; disabling of endogenous genes which encode catabolic enzymes for the starter and/or extender units; incorporation of expression systems for enzymes required for post translational modification of the synthases, such as phosphopantetheinyl transferase; and incorporation of enzymes which enhance the levels of starter and/or extender units. The particular combination of modifications required to adapt the host will vary with the nature of the polyketide desired and with the nature of the host itself.

Thus, in one aspect, the invention is directed to microbial host cells which are genetically modified for enhanced synthesis of at least one polyketide wherein said modification comprises incorporation of at least one expression system for producing a protein that catalyzes the production of starter and/or extender units and/or disabling at least one endogenous pathway for catabolism of starter and/or extender units.

Additional modifications may also be made, such as incorporating at least one expression system for a polyketide synthase protein and, if necessary, incorporating at least one expression system for a phosphopantetheinyl transferase.

In other aspects, the invention is directed to methods of preparing polyketides, including complete polyketides, in the modified cells of the invention. A preferred embodiment is a method to synthesize 6-dEB or other complete polyketides in *E. coli*.

In still another aspect, the invention is directed to a method to assess the results of gene shuffling or random mutagenesis of polyketide synthase genes by taking advantage of the high transformation efficiency of *E. coli*.

MODES OF CARRYING OUT THE INVENTION

In the illustrative example below, *E. coli* is modified to effect the production of 6-dEB, the polyketide precursor of erythromycin. The three proteins required for this synthesis, DEBS1, DEBS2 and DEBS3 are known and the genes encoding them have been cloned and sequenced. However, a multiplicity of additional PKS genes have been cloned and sequenced as well, including those encoding enzymes which produce the polyketide precursors of avermectin, oleandomycin, epothilone, megalomycin, picromycin, FK506, FK520, rapamycin, tylosin, spinosyl, and many others. In addition, methods to modify native PKS genes so as to alter the nature of the polyketide produced have been described. Production of hybrid modular PKS proteins and synthesis systems is described and claimed in U.S. Pat. No. 5,962,290. Methods to modify PKS enzymes so as to permit efficient incorporation of diketides is described in U.S. Pat. No. 6,080,555. Methods to modify PKS enzymes by mixing and matching individual domains or groups of domains is described in U.S. Ser. No. 09/073,538. Methods to alter the specificity of modules of modular PKS's to incorporate particular starter or extender units are described in U.S. Pat. No. 6,221,641. Improved methods to prepare diketides for incorporation into polyketides is described in U.S. Ser. No. 09/492,733. Methods to mediate the synthesis of the polyketide chain between modules are described in U.S. Ser. No. 09/500,747. The contents of the foregoing patents and patent applications are incorporated herein by reference.

Thus, a selected host may be modified to include any one of many possible polyketide synthases by incorporating therein appropriate expression systems for the proteins included in such synthases. Either complete synthases or partial synthases may be supplied depending on the product desired. If the host produces polyketide synthase natively, and a different polyketide from that ordinarily produced is desired, it may be desirable to delete the genes encoding the native PKS. Methods for such deletion are described in U.S. Pat. No. 5,830,750, which is incorporated herein by reference.

For hosts which do not natively produce polyketides, the enzymes that tailor polyketide synthases may be lacking or deficient, so that in addition to supplying the expression systems for the polyketide synthases themselves, it may be necessary to supply an expression system for these enzymes. One enzyme which is essential for the activity of PKS is a phosphopantetheinyl transferase. The genes encoding these transferases have been cloned and are available. These are described in U.S. Pat. No. 6,579,695. The contents of this document are incorporated herein by reference.

Depending on the host selected, such hosts may natively include genes which produce proteins that catabolize desired starter and/or extender units. One example includes the prp operon wherein the proteins encoded by subunits A-D catabolize exogenous propionate. The enzyme encoded by prp E is desirable however as it is a propionyl CoA synthetase. The portions of the operon encoding catabolizing enzymes are advantageously disabled in modifying *E. coli*. Similar operons in other hosts may be disabled as needed.

In general, in all cases, enzymes that enhance the production of starter and/or extender units, and any enzymes required for activation of these production enzymes need to be incorporated in the cells by modifying them to contain expression systems for these proteins.

In one embodiment of this aspect, advantage is taken of the matABC operon, which was recently cloned from *Rhizobium trifoli* (An, J. H., et al., *Eur. J. Biochem.* (1998)15: 395–402). There are three proteins encoded by this operon.

MatA encodes a malonyl-CoA decarboxylase, which normally catalyzes the reaction: malonyl-CoA→acetyl-CoA+$CO_2$.

MatB encodes a malonyl-CoA synthetase which catalyzes the reaction: malonic acid+CoASH→malonyl-CoA (in an ATP dependent reaction).

MatC encodes a malonate transporter which is believed to be responsible for transport of malonic acid across the cell membrane.

These enzymes are demonstrated herein to be somewhat promiscuous with respect to substrate in their ability to catalyze the reactions shown. Thus, in addition to malonyl-CoA and malonic acids (for MatA and MatB respectively) as substrates, these enzymes can also utilize methylmalonyl-CoA and methylmalonic acid; ethylmalonyl-CoA and ethylmalonic acid; propylmalonyl-CoA and propylmalonic acid and the like. Thus, these enzymes can be used to provide a variety of starter and extender units for synthesis of desired polyketides.

In another embodiment of this aspect, homologs of matB and matC derived from *S. coelicolor* (GenBank accession No. AL163003) can be used.

Also useful in supplying substrates for extender units is the gene encoding propionyl CoA carboxylase. This carboxylase enzyme is a dimer encoded by the pccB and accA2 genes which have been characterized from *Streptomyces coelicolor* A3 by Rodriguez, E., et al., *Microbiology* (1999) 145:3109–3119. A biotin ligase is needed for activation of these proteins. The typical substrate for this enzyme is propionyl-CoA which is then converted to methylmalonyl-CoA; a reaction which is summarized as propionyl-CoA+$CO_2$→methylmalonyl-CoA (an ATP dependent reaction).

Other acyl-CoA substrates may also be converted to the corresponding malonyl-CoA products.

In addition to providing modified host cells that are efficient in producing polyketides, the polyketide synthases, their activation enzymes, and enzymes which provide starter and/or extender units can be used in in vitro systems to produce the desired polyketides. For example, the enzymes malonyl-CoA decarboxylase and/or malonyl-CoA synthetase such as those encoded by the matABC operon and/or propionyl-CoA carboxylase such as that encoded by the pccB and accA2 genes can be used in in vitro cultures to convert precursors to suitable extender and starter units for a desired PKS to effect synthesis of a polyketide in a cell-free or in in vitro cell culture system. Purified MatB is particularly advantageously used for the preparative cell free production of polyketides, since CoA thioesters are the most expensive components in such cell-free synthesis systems. Alternatively, as set forth above, these genes are used (in any suitable combination) in a general strategy for production by cells in culture of these substrates. MatB and MatC can be used to effect production of any alpha-carboxylated CoA thioester where the corresponding free acid can be recognized as a substrate by MatB. The MatA protein may also be used to supplement in vitro or in vivo levels of starter units such as acetyl-CoA and propionyl-CoA. The genes encoding propionyl-CoA carboxylase can also be used to provide the enzyme to synthesize suitable extender units in vivo.

Thus, the invention includes a method to enhance the production of a polyketide, including a complete polyketide in a microbial host, which method comprises providing said host with an expression system for an enzyme which enhances the production of starter and/or extender units used in constructing the polyketide. A "complete" polyketide is a polyketide which forms the basis for an antibiotic, such as the polyketides which are precursors to erythromycin, megalomycin, and the like. The enzymes include those encoded by the matABC operon and their homologs in other organisms as well as the pccB and accA2 genes encoding propionyl carboxylase and their homologs in other organisms. In another aspect, the invention is directed to a method of enhancing production of polyketides in cell-free systems by providing one or more of these enzymes to the cell-free system.

The invention is also directed to cells modified to produce the enzymes and to methods of producing polyketides using these cells, as well as to methods of producing polyketides using cell-free systems.

The invention also includes a method to enhance polyketide production in a microbial system by supplementing the medium with a substrate for an endogenous enzyme which converts this substrate to a starter or extender unit.

The invention also includes a method to produce polyketides in microbial hosts containing modifications to assist polyketide production, such as disarming of the endogenous genes which encode proteins for catabolism of required substrates, by supplying these cells with synthetic precursors, such as diketide precursors.

The polyketide produced may be one normally produced by the PKS and may exist in nature; in this case the presence of the gene encoding the starter/extender production-enhancing enzyme in vivo or of the enzyme itself in cell free systems may simply enhance the level of production. In addition, the PKS may be a modified PKS designed to produce a novel polyketide, whose production may be enhanced in similar fashion. Because of the ability of the enzymes described herein to accept a wide range of substrates, extender units and starter units can be provided based on a wide range of readily available reagents. As stated above, diketide starting materials may also be supplied.

The invention thus also includes the various other modifications of microbial hosts described above to permit or enhance their production of polyketides and to methods of producing polyketides using such hosts.

The ability to modify hosts such as *E. coli* and other procaryotes such as *Bacillus* to permit production of polyketides in such hosts has numerous advantages, many of which reside in the inherent nature of *E. coli*. One important advantage resides in the ease with which *E. coli* can be transformed as compared to other microorganisms which natively produce polyketides. One important application of this transformation ease is in assessing the results of gene shuffling of polyketide synthases. Thus, an additional aspect of the invention is directed to a method to assess the results of polyketide synthase gene shuffling which method comprises transfecting a culture of the *E. coli* modified according to the invention with a mixture of shuffled polyketide synthases and culturing individual colonies. Those colonies which produce polyketides contain successfully shuffled genes.

In addition to modifying microbial hosts, especially procaryotic hosts, to produce polyketides, these hosts may further be modified to produce the enzymes which "tailor" the polyketides and effect their conversion to antibiotics. Such tailoring reactions include glycosylation, oxidation, hydroxylation and the like.

To effect production of the polyketides in a microbial host, it is preferable to permit substantial growth of the culture prior to inducing the enzymes which effect the synthesis of the polyketides. Thus, in hosts which do not natively produce polyketides, the required expression systems for the PKS genes are placed under control of an inducible promoter, such as the T7 promoter which is induced by IPTG. There is a plethora of suitable promoters which are inducible in a variety of such microbial hosts. Other advantageous features of the modified host, such as the ability to synthesize starters or extenders, may also be under inducible control. Finally, precursors to the starting materials for polyketide synthase may be withheld until synthesis is desired. Thus, for example, if the starting materials are derived from propionate, propionate can be supplied at any desired point during the culturing of the cells. If a diketide or triketide starting material is used, this too can be withheld until the appropriate time. Prior to addition of the precursor, a minimal medium may be used and alternate carbon sources employed to supply energy and materials for growth.

As described above, the invention provides methods for both in vitro and in vivo synthesis of any arbitrarily chosen polyketide where the in vivo synthesis may be conducted in any microbial, especially procaryotic host. The procaryotic host is typically of the genus *Bacillus, Pseudomonas, Flavobacterium*, or more typically *Escherichia*, in particular *E. coli*. Whether in vitro or in vivo synthesis is employed, it may be necessary to supply one or more of a suitable polyketide synthase (which may be native or modified), one or more enzymes to produce starter and/or extender units, typically including converting the free acid to the CoA derivative, and, if the foregoing enzymes are produced in a host, tailoring enzymes to activate them. In addition, for in vivo synthesis, it may be necessary to disarm catabolic enzymes which would otherwise destroy the appropriate starting materials.

With respect to production of starting materials, the genes of the matABC operon and the genes encoding propionyl carboxylase can be employed to produce their encoded proteins for use in cell free polyketide synthesis and also to modify recombinant hosts for production of polyketides in cell culture. These genes and their corresponding encoded products are useful to provide optimum levels of substrates for polyketide synthase in any host in which such synthesis is to be effected. The host may be one which natively produces a polyketide and its corresponding antibiotic or may be a recombinantly modified host which either does not natively produce any polyketide or which has been modified to produce a polyketide which it normally does not make. Thus, microorganism hosts which are useable for the synthesis of polyketides include various strains of *Streptomyces*, in particular *S. coelicolor* and *S. lividans*, various strains of *Myxococcus*, industrially favorable hosts such as *E. coli, Bacillus, Pseudomonas* or *Flavobacterium*, and other microorganisms such as yeast. These genes and their corresponding proteins are useful in adjusting substrate levels for polyketide synthesis generally.

Substrate Specificity and Polyketide Design

These genes and their products are particularly useful because of the ability of the enzymes to utilize a range of starting materials. Thus, in general, propionyl carboxylase converts a thioester of the formula $R_2$—CH—CO—SCoA, where each R is H or an optionally substituted alkyl or other optionally substituted hydrocarbyl group to the corresponding malonic acid thioester of the formula $R_2C(COOH)$ COSCoA. Other thioesters besides the natural co-enzyme A thioester may also be used such as the N-acyl cysteamine thioesters. Similarly, the product of the matB gene can convert malonic acid derivatives of the formula $R_2C(COOH)_2$ to the corresponding acyl thioester, where each R is independently H or optionally substituted hydrocarbyl. A preferred starting material is that wherein R is alkyl (1–4 C), preferably $RCH(COOH)_2$. For in vivo systems, it may be advantageous to include the matC gene to ensure membrane transport of the starting malonic acid related material. The matA gene encodes a protein which converts malonyl-CoA substrates of the formula $R_2C(COOH)COSCoA$ to the corresponding acyl-CoA of the formula $R_2CHCOSCoA$, where R is defined as above, for use as a starter unit.

Typically, the hydrocarbyl groups referred to above are alkyl groups of 1–8 C, preferably 1–6 C, and more preferably 1–4 C. The alkyl groups may be straight chain or branch chain, but are preferably straight chain. The hydrocarbyl groups may also include unsaturation and may further contain substituents such as halo, hydroxyl, methoxyl or amino or methyl or dimethyl amino. Thus, the hydrocarbyl groups may be of the formula $CH_3CHCHCH_2$; $CH_2CHCH_2$; $CH_3OCH_2CH_2CH_2$; $CH_3CCCH_2$; $CH_3CH_2CH_2CH_2CH_2$; and the like.

The substituted alkyl groups are also 1–8 C in the backbone chain, preferably 1–6 C and more preferably 1–4 C. The alkenyl and alkynyl hydrocarbyl groups contain 2–8 C, preferably 2–6 C, and more preferably 2–4 C and may also be branched or straight chain, preferably straight chain.

Further variability can be obtained by supplying as a starting material a suitable diketide. The diketide generally of the formulas such as those set forth in U.S. Pat. No. 6,500,960, incorporated herein by reference. A variety of substituents can then be introduced. Thus, the diketide will be of the general formula $R'CH_2CHOHCR_2COSNAc$ wherein R is defined as above, and R' can be alkyl, 1–8 C, aryl, aryl alkyl, and the like. SNAc represents a thioester of N-acetyl cysteamine, but alternative thioesters could also be used.

For either in vivo or in vitro production of the polyketides, acyl transferase domains with desired specificities can be incorporated into the relevant PKS. Methods for assuring appropriate specificity of the AT domains is described in detail in U.S. Pat. No. 6,221,641, the contents of which are incorporated herein by reference, to describe how such domains of desired specificity can be created and employed. Also relevant to the use of these enzymes in vitro or the genes in vivo are methods to mediate polyketide synthase module effectiveness by assuring appropriate transfer of the growing polyketide chain from one module to the next. Such methods are described in detail in U.S. Ser. No. 09/500,747 filed 9 Feb. 2000, the contents of which are incorporated herein by reference for this description.

The nucleotide sequences encoding a multiplicity of PKS permits their use in recombinant procedures for producing a desired PKS and for production of the proteins useful in postmacrolide conversions, as well as modified forms thereof. For example, the nucleotide sequences for genes related to the production of erythromycin is disclosed in U.S. Pat. No. 6,004,787 and U.S. Pat. No. 5,998,194; for avermectin in U.S. Pat. No. 5,252,474; for FK506 in U.S. Pat. No. 5,622,866; for rifamycin in WO98/7868; for spiramycin in U.S. Pat. No. 5,098,837. These are merely examples. Portions of, or all of, the desired coding sequences can be synthesized using standard solid phase synthesis methods such as those described by Jaye et al., *J Biol Chem* (1984) 259:6331 and which are available commercially from, for example, Applied Biosystems, Inc.

A portion of the PKS which encodes a particular activity can be isolated and manipulated, for example, by using it to replace the corresponding region in a different modular PKS. In addition, individual modules of the PKS may be ligated into suitable expression systems and used to produce the portion of the protein encoded by the open reading frame and the protein may then be isolated and purified, or which may be employed in situ to effect polyketide synthesis. Depending on the host for the recombinant production of the module or an entire open reading frame, or combination of open reading frames, suitable control sequences such as promoters, termination sequences, enhancers, and the like are ligated to the nucleotide sequence encoding the desired protein. Suitable control sequences for a variety of hosts are well known in the art.

The availability of these nucleotide sequences expands the possibility for the production of novel polyketides and their corresponding antibiotics using host cells modified to contain suitable expression systems for the appropriate enzymes. By manipulating the various activity-encoding regions of a donor PKS by replacing them into a scaffold of a different PKS or by forming hybrids instead of or in addition to such replacements or other mutagenizing alterations, a wide variety of polyketides and corresponding antibiotics may be obtained. These techniques are described, for example, in U.S. Pat. No. 6,558,942, incorporated herein by reference.

A polyketide synthase may be obtained that produces a novel polyketide by, for example, using the scaffolding encoded by all or the portion employed of a natural synthase gene. The synthase will contain at least one module that is functional, preferably two or three modules, and more preferably four or more modules and contains mutations, deletions, or replacements of one or more of the activities of these functional modules so that the nature of the resulting polyketide is altered. This description applies both at the protein and genetic levels. Particularly preferred embodiments include those wherein a KS, AT, KR, DH or ER has been deleted or replaced by a version of the activity from a different PKS or from another location within the same PKS. Also preferred are derivatives where at least one noncondensation cycle enzymatic activity (KR, DH or ER) has been deleted or wherein any of these activities has been mutated so as to change the ultimate polyketide synthesized.

Thus, in order to obtain nucleotide sequences encoding a variety of derivatives of the naturally occurring PKS, and a variety of polyketides, a desired number of constructs can be obtained by "mixing and matching" enzymatic activity-encoding portions, and mutations can be introduced into the native host PKS gene cluster or portions thereof.

Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion (See, e.g., Kunkel, T. A. *Proc Natl Acad Sci USA* (1985) 82:448; Geisselsoder et al. *BioTechniques* (1987) 5:786.) or by a variety of other art-known methods.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants or by damaging plasmid DNA in vitro with chemicals.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER would correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT application WO 96/40968.

Finally, polyketide synthase genes, like DNA sequences in general, in addition to the methods for systematic alteration and random mutagenesis outlined above, can be modified by the technique of "gene shuffling" as described in U.S. Pat. No. 5,834,458, assigned to Maxygen, and U.S. Pat. Nos. 5,830,721, 5,811,238 and 5,605,793, assigned to Affymax. In this technique, DNA sequences encoding bPKS are cut with restriction enzymes, amplified, and then re-ligated. This results in a mixture of rearranged genes which can be assessed for their ability to produce polyketides. The ability to produce polyketides in easily transformed hosts, such as *E. coli*, makes this a practical approach.

There are five degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, or ethyl malonyl, etc. Third, the loading domain specificity will also have an effect on the resulting carbon skeleton of the polyketide. Thus, the loading domain may use a different starter unit, such as acetyl, propionyl, butyryl and the like. Fourth, the oxidation state at various positions of the polyketide will be determined by the dehydratase and reductase portions of the modules. This will determine the presence and location of ketone, alcohol, double bonds or single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Second, the specificity of the ketoreductase will determine the chirality of any β—OH. Finally, the enoyl reductase specificity for substituted malonyls as extender units will influence the result when there is a complete KR/DH/ER available.

One useful approach is to modify the KS activity in module 1 which results in the ability to incorporate alternative starter units as well as module 1 extended units. This approach was illustrated in PCT application US/96/11317, incorporated herein by reference, wherein the KS-1 activity was inactivated through mutation. Polyketide synthesis is then initiated by feeding chemically synthesized analogs of module 1 diketide products. The methods of the invention can then be used to provide enhanced amount of extender units.

Modular PKSs have relaxed specificity for their starter units (Kao et al. *Science* (1994), supra). Modular PKSs also exhibit considerable variety with regard to the choice of extender units in each condensation cycle. The degree of β-ketoreduction following a condensation reaction has also been shown to be altered by genetic manipulation (Donadio et al. *Science* (1991), supra; Donadio, S. et al. *Proc Natl Acad Sci USA* (1993) 90:7119–7123). Likewise, the size of the polyketide product can be varied by designing mutants with the appropriate number of modules (Kao, C. M. et al. *J Am Chem Soc* (1994) 116:11612–11613). Lastly, these enzymes are particularly well-known for generating an impressive range of asymmetric centers in their products in a highly controlled manner. The polyketides and antibiotics produced by the methods of the present invention are typically single stereoisomeric forms. Although the compounds of the invention can occur as mixtures of stereoisomers, it is more practical to generate individual stereoisomers using the PKS systems.

The polyketide products of the PKS may be further modified, typically by hydroxylation, oxidation and/or glycosylation, in order to exhibit antibiotic activity.

Methods for glycosylating the polyketides are generally known in the art; the glycosylation may be effected intracellularly by providing the appropriate glycosylation enzymes or may be effected in vitro using chemical synthetic means as described in U.S. Ser. No. 09/073,538 incorporated herein by reference.

The antibiotic modular polyketides may contain any of a number of different sugars, although D-desosamine, or a close analog thereof, is most common. For example, erythromycin, picromycin, narbomycin and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al. *J Am Chem Soc* (1975) 97:3512, 3513. Other, apparently more stable, donors include glycosyl fluorides, thioglycosides, and trichloroacetimidates; Woodward, R. B. et al. *J Am Chem Soc* (1981) 103:3215; Martin, S. F. et al. *Am Chem Soc* (1997) 119: 3193; Toshima, K. et al. *J Am Chem Soc* (1995) 117:3717; Matsumoto, T. et al. *Tetrahedron Lett* (1988) 29:3575.

Glycosylation can also be effected using the macrolides as starting materials and using mutants of *S. erythraea* that are unable to synthesize the macrolides to make the conversion.

In general, the approaches to effecting glycosylation mirror those described above with respect to hydroxylation. The purified enzymes, isolated from native sources or recombinantly produced may be used in vitro. Alternatively, glycosylation may be effected intracellularly using endogenous or recombinantly produced intracellular glycosylases. In addition, synthetic chemical methods may be employed.

If the hosts ordinarily produce polyketides, it may be desirable to modify them so as to prevent the production of endogenous polyketides by these hosts. Such hosts have been described, for example, in U.S. Pat. No. 5,672,491, incorporated herein by reference, which describes *S. coelicolor* CH999 used in the examples below. In such hosts, it may not be necessary to provide enzymatic activity for posttranslational modification of the enzymes that make up the recombinantly produced polyketide synthase; these hosts generally contain suitable enzymes, designated holo-ACP synthases, for providing a pantetheinyl residue needed for functionality of the synthase. However, in hosts such as yeasts, plants, or mammalian cells which ordinarily do not produce polyketides, it may be necessary to provide, also typically by recombinant means, suitable holo-ACP synthases to convert the recombinantly produced PKS to functionality. Provision of such enzymes is described, for example, in PCT application WO 98/27203, incorporated herein by reference.

Again, depending on the host, and on the nature of the product desired, it may be necessary to provide "tailoring enzymes" or genes encoding them, wherein these tailoring enzymes modify the macrolides produced by oxidation, hydroxylation, glycosylation, and the like.

The encoding nucleotide sequences are operably linked to promoters, enhancers, and/or termination sequences which operate to effect expression of the encoding nucleotide sequence in host cells compatible with these sequences; host cells modified to contain these sequences either as extrachromosomal elements or vectors or integrated into the chromosome, and methods to produce PKS and post-PKS enzymes as well as polyketides and antibiotics using these modified host cells.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in a appropriate host. However, simple cloning vectors may be used as well.

Particularly useful control sequences are those which themselves, or using suitable regulatory systems, activate expression during transition from growth to stationary phase in the vegetative mycelium. The system contained in the illustrative plasmid pRM5, i.e., the actI/actIII promoter pair and the actII-ORF4, an activator gene, is particularly preferred. Particularly preferred hosts are those which lack their own means for producing polyketides so that a cleaner result is obtained. Illustrative host cells of this type include the modified *S. coelicolor* CH999 culture described in PCT application WO 96/40968 and similar strains of *S. lividans*.

Methods for introducing the recombinant vectors of the present invention into suitable hosts are known to those of skill in the art and typically include the use of CaCl2 or other agents, such as divalent cations, lipofection, DMSO, protoplast transformation and electroporation.

As disclosed in U.S. Pat. No. 6,033,883, incorporated herein by reference, a wide variety of hosts can be used, even though some hosts natively do not contain the appropriate post-translational mechanisms to activate the acyl carrier proteins of the synthases. These hosts can be modified with the appropriate recombinant enzymes to effect these modifications.

Starting Material Enhancement and Variation

Thus, proteins (and their encoding sequences) wherein the proteins catalyze the production of starter and/or extender units can be used to enhance the production of polyketides by providing a considerable variety of these starter and extender units at higher levels than would ordinarily be produced. Because the proteins catalyze reactions using a variety of substrates, they are versatile tools in enhancing the availability of starter and extender units for a wide variety of PKS, whether modified or unmodified. As stated above, particularly useful are the products of the matABC operon (or analogous operons in other species) and the propionic carboxylase encoded by the pccB and accA2 genes (or their analogs in other species). These enzymes and their encoding sequences are useful in view of Applicants' discovery that the matABC operon and the propionic carboxylase-encoding genes provide enzymes which not only carry out the required reactions on a variety of substances, but also do so with the production of products with the stereochemistry required for use in polyketide synthesis.

The ability of the genes described herein to provide appropriate starter and extender units was established as described below.

EXAMPLE 1

Production of Malonyl CoA and 2S-Methylmalonyl CoA Using the CoA Synthetase

*E. coli* strain L8 has a temperature-sensitive mutation in the acetyl-CoA carboxylase gene such that malonyl-CoA cannot be produced from acetyl-CoA at 37° C. However, the gene product is able to effect this conversion at 30° C. See Harder, M. E., et al., *Proc. Natl. Acad. Sci.* (1972) 69:3105–3109. Since acetyl-CoA carboxylase conversion of acetyl-CoA into malonyl-CoA is the only known route for malonyl-CoA production in *E. coli*, and since malonyl-CoA is essential for fatty acid biosynthesis, this mutant strain of *E. coli* can grow at 30° C., but not at 37° C. A transformant of L8 carrying the matABC operon is produced by transforming with the plasmid pMATOP2 which contains the matA, matB and matC genes under control of their native promoter and is described in An, J. H., et al., *Eur. J. Biochem.* (1998) 257:395–402. This transformant is still unable to grow at 37° C. in the absence of malonic acid; however, addition of 1–5 mM malonic acid to the medium permits it to grow at this temperature. (In the absence of the plasmid, malonic acid is unable to support growth at 37° C.) The concentration of the extracellular malonic acid is important, however, as increasing the concentration to 40 mM results in an absence of growth, possibly due to a metabolic imbalance caused by overproduction of malonyl CoA in comparison to the amount of coenzyme A available. Lethality was also induced in XL1-Blue (a wild-type strain of *E. coli*) in the presence of the plasmid carrying the matABC operon and high concentrations of methylmalonic acid.

Nevertheless, the results set forth above demonstrate that the protein encoded by matB produces malonyl-CoA in vivo under physiological conditions as long as free malonic acid is available; and transported into the cells by the protein encoded by matC. Thus, the matBC genes can be used to supplement malonyl-CoA availability in an *E. coli* cell in which complex polyketides are to be produced by feeding malonic acid.

In addition to converting malonic acid into malonyl-CoA, MatB has also been shown to convert methylmalonic acid into methylmalonyl-CoA. However the stereochemistry of the resulting product has not been reported. This is important, because modular polyketide synthases are known to only accept one isomer of methylmalonyl-CoA, namely 2S-methylmalonyl-CoA (Marsden, A. F., et al., *Science* (1994) 263:378–380). To investigate whether MatB can make the correct isomer of methylmalonyl-CoA, construct encoding a glutathione-S-transferase fusion (GST-MatB) was used to produce this protein. See An, J. H., et al., *Biochem. J.* (1999) 344:159–166. The GST-MatB protein was purified according to standard protocols as described and mixed with (module 6+TE) of the erythromycin polyketide synthase, also expressed in *E. coli* as described by Gokhale, R. S., et al., *Science* (1999) 284:482–485.

In earlier studies, Applicants have established the activity of (module 6+TE) by demonstrating its ability to catalyze the following reaction in vitro.

N-acetylcysteamine thioester of (2S, 3R)-2-methyl-3-hydroxy-pentanoic acid+2 (RS)-methylmalonyl-CoA+NADPH→(2R,3S,4S,5R)-2,4-dimethyl-3,5-dihydroxy-n-heptanoic acid δ-lactone+NADP$^+$.

The methylmalonic thioester product obtained using methylmalonic acid as the substrate for GST-MatB provides the correct stereochemistry to serve as the source of the extender unit in this reaction. More specifically, to generate the substrate for the above polyketide synthesis in situ, the following reaction mixture (containing 6+TE and GST-MatB) was prepared in a reaction buffer of 100 mM Na Phosphate (pH7) buffer, 1 mM EDTA, 2.5 mM DTT and 20% glycerol:

40 mM methylmalonic acid (pH 6)
16.6 mM MgCl$_2$
5 mM ATP
5 mM CoASH
13.3 mM NADPH
1 mM N-acetylcysteamine thioester of (2S, 3R)-2-methyl-3-hydroxypentanoic acid (prepared in radioactive form).

After 4 hrs, the reaction was quenched and extracted with ethyl acetate (extracted twice with three times the reaction volume). The samples were dried in vacuo and subjected to thin layer chromatography analysis.

A positive control was performed under identical conditions to those described earlier—i.e., conditions wherein (RS)-methylmalonyl-CoA was substituted for the combination of methylmalonic acid, MgCl$_2$, ATP, CoA SH, and GST-MatB. A negative control included all of the components listed above except for the GST-MatB fusion protein. The results demonstrated that the two-enzyme system described above is able to produce the expected product in quantities comparable to the positive control reaction. This confirms that MatB synthesizes the correct isomer of methylmalonyl-CoA.

Thus, MatB/MatC is useful to synthesize both malonyl-CoA and 2S-methylmalonyl-CoA in vivo for polyketide biosynthesis. This is the first instance of engineering *E. coli* with the ability to produce 2S-methylmalonyl-CoA in vivo under physiological conditions. Moreover, co-expression of matA in vivo should allow conversion of methylmalonyl-CoA into propionyl-CoA, thereby supplementing available sources of this starter unit.

EXAMPLE 2

Ability of Propionyl CoA Carboxylase to Generate 2S-Methylmalonyl CoA

To utilize the propionyl carboxylase gene from *S. coelicolor* described above, an *E. coli* expression host (BL-21 (DE3)) was prepared using the method developed by Hamilton, C. M., et al., *J. Bacteriol.* (1989) 171:4617–4622. The new strain (BAP1) contains a phosphopantethiene-transferase gene (the sfp gene) from *Bacillus subtilis* integrated into the prp operon of *E. coli*. The T7 promoter drives sfp expression. In the recombination procedure, the prpE gene was also placed under control of the T7 promoter, but the rest of the operon was removed. This genetic alteration would ideally provide three features: 1) the expression of the sfp protein needed for post-translational modification of the DEBS and potentially other polyketide synthases (PKSs); 2) the expression of the prpE protein, a putative propionyl-CoA synthetase theoretically capable of ligating CoASH to propionate; and 3) a cellular environment that is no longer able to metabolize propionyl-CoA as a carbon/energy source.

First, it was verified that the BAP1 strain, by virtue of its production of the product of the sfp gene was able to effect phosphopantetheinylation of a PKS produced in these cells. BAP1 was transfected with a plasmid comprising an expression system for module 6+TE and the activity of the module produced was compared to the activity of the module produced recombinantly in BL-21 (DE3) cells where the sfp gene was plasmid borne. These levels were comparable. In contrast, when expressed alone in BL-21 (DE3), module 6+TE showed no activity. Additionally, BAP1 was confirmed for its inability to grow on propionate as a sole carbon source (a property exhibited by *E. coli* strains such as BL21 (DE3)). BAP1 is a preferred host for the heterologous expression of polyketide synthases in conjunction with enzymes such as MatBC and propionyl-CoA carboxylase.

The propionyl-CoA carboxylase enzyme was expressed in *E. coli* under the T7 promoter. The product enzyme was able to supply substrate for module 6+TE in vitro. This was demonstrated using the coupling of the methylmalonyl-CoA thioester product of the propionyl CoA carboxylase enzyme to the N-acetyl cysteamine thioester of (2S,2R)$_2$-methyl-3-hydroxypentanoic acid. The pccB and accA2 genes described above which encode the components of the propionyl-CoA carboxylase, were expressed and the products individually purified according to standard procedures. Initially, the pccB and accA2 subunits were allowed to complex on ice in 150 mM phosphate (pH7) and 300 μg BSA. After 1 hour, the following substrates were added to a volume of 100 μl and incubated for an additional 30 minutes at 30° C.:

1 mM propionyl-CoA
50 mM sodium bicarbonate
3 mM ATP
5 mM MgCl$_2$

Module 6+TE was then added with the following final set of reagents to give 200 μl total and allowed to react for an additional hour at 30° C.:

10% glycerol
1.25 mM DTT
0.5 mM EDTA
4 mM NADPH 2 mM N-acetylcysteamine thioester of (2S, 3R)-2-methyl-3-hydroxypentanoic acid (prepared in radioactive form).

The reaction was quenched and extracted as described above, and showed formation of expected product. A positive control included racemic malonyl-CoA. When either ATP or sodium bicarbonate was removed from the reaction, no product was formed. The propionyl-CoA carboxylase thus produces a substrate suitable for polyketide synthase activity. This is particularly useful for polyketide production, especially in conjunction with the new expression host mentioned above, BAP1.

The DEBS protein DEBS1+TE is produced by pRSG32. DEBS1 shows the weakest expression of the three DEBS proteins and, until recently, the enzyme showed no in vitro activity. However, by growing E. coli containing pRSG32 in M9 minimal medium, and inducing protein expression at 22° C., DEBS1+TE activity is now reproducibly observed.

Plasmids pRSG32 (DEBS1+TE) and p132 (a plasmid containing the α and β components of propionyl-CoA carboxylase) were cotransfected into BAP1. Cultures of 10 ml M9 minimal media were grown to mid-log phase levels and concentrated to 1 ml for induction with IPTG and the addition of 0.267 mM $^{14}$C-propionate. The samples were then incubated at 22° C. for 12–15 hours. The culture supernatant was then extracted with ethyl acetate for analytical TLC. A product ran with the expected positive control and this same product was undetectable when using either wild type BL-21 (DE3) or removing p132. Thus, the carboxylase forms the correct stereoisomer.

In addition, 100 ml cultures of M9 minimal media containing BAP1 transformed with pRSG32, p132, and pCY214 (a biotin ligase included to aid biotin's attachment to the α subunit of the propionyl-CoA carboxylase) were grown to mid-log phase for induction with IPTG and the addition of 100 mg/L $^{13}$C-propionate. Upon extraction of the culture supernatant and concentration of the sample, $^{13}$C-NMR confirmed the location of the expected enriched product peaks. A subsequent negative control using BL-21 (DE3) failed to yield the same spectrum. In addition to demonstrating the ability of E. coli to make complex polyketides in vivo, these results also suggest that the prpE protein programmed to express in BAP1 is active.

EXAMPLE 3

Enhanced Production of 6-dEB in S. coelicolor

The presence of the matB and matC genes was also able to enhance the recombinant production of 6-dEB in S. coelicolor which had been recombinantly modified to produce this polyketide by insertion of the DEBS gene complex on the vector pCK7. The matB and matC genes were expressed in a recombinant strain of Streptomyces coelicolor that produces 50 mg/L 6-deoxyerythronolide B by virtue of plasmid borne DEBS genes. The matB and matC genes were inserted immediately downstream of DEBS genes on pCK7. In more detail, the source of the matBC genes is pFL482, a derivative of PCR-Blunt (Invitrogen) containing a 5 kb BglII/HindIII fragment from pMATOP2 which carries the matBC genes. The NsiI fragment of pFL482 containing the matBC genes was cloned into the unique NsiI site of pCK7 in the same direction as the DEBS genes to yield pFL494. Upon transformation of plasmid pFL494 into S. coelicolor CH999, macrolide titer increases of 100–300% were obtained in the presence of exogenous methylmalonate (0.1–1 g/L).

In more detail, cultures of S. coelicolor CH999 with or without plasmid pCK7 or pFL494 were grown in flasks using R6 medium (sucrose, 103 g/L; $K_2SO_4$, 0.25 g/L; $MgCl_2$ $6H_2O$, 10.12 g/L; sodium propionate, 0.96 g/L; casamino acids (Difco), 0.1 g/L; trace elements solution, 2 mL/L; yeast extract (Fisher), 5 g/L; pH 7) supplemented with bis-tris propane buffer (28.2 g/L). Trace elements solution contained $ZnCl_2$, 40 mg/L; $FeCl_3.6H_2O$, 200 mg/L; $CuCl_2.2H_2O$, 10 mg/L; $MnCl_2.4H_2O$, 10 mg/L; $Na_2B_4O_7.10H_2O$, 10 mg/L; $(NH_4)_6Mo_7O_{24}.4H_2O$. All media were supplemented with 50 mg/L thiostrepton (Calbiochem) to select for plasmid-containing cells, and with mL/L Antifoam B (JT Baker) for control of foam. Thiostrepton was dissolved in DMSO prior to addition to cultures, giving a final DMSO concentration of approximately 1 mL/L of medium.

Seed cultures for the fermentation were prepared by inoculation of 50 mL medium, followed by growth for two days at 240 rpm and 30° C. in 250 mL baffled flasks (Bellco). These seed cultures were then used to inoculate 50 mL medium in the presence or absence of 1 g/L methylmalonate in 250-mL baffled flasks at 5% of final volume. All flask cultures were run in duplicate and sampled daily. The entire experiment was repeated once to ensure batch-to-batch reproducibility of the results.

Quantitation of 6-dEB and 8,8a-deoxyoleandolide was carried out using a Hewlett-Packard 1090 HPLC equipped with an Alltec 500 evaporative light scattering detector. HPLC samples were first centrifuged 5 min at 12,000×g to remove insolubles. The supernatant (20 μL) was applied onto a 4.6×10 mm column (Inertsil, C 18 ODS3, 5 μm), washed with water (1 ml/min for 2 min), and finally eluted onto the main column (4.6×50 mm, same stationary phase and flow rate) with a 6-min gradient starting with 100% water and ending with 100% acetonitrile. 100% acetonitrile was then maintained for one min. Under these conditions, 6-dEB eluted at 6.2 minutes and 8.8a-deoxyoleandolide at 5.8 min. Standards were prepared from 6-dEB purified from fermentation broth. Quantitation error was estimated to be±10%.

As described above, S. coelicolor CH999 either containing pCK7 or containing pFL494 were compared for their productivity of 6-dEB and 8,8a-deoxyoleandolide.

The results show the following:

1. Cell density was substantially the same for both strains.

2. The production of both 6-dEB and 8,8a-deoxyoleandolide is dramatically enhanced in CH999/pFL494 as compared to CH999/pCK7, whether measured in terms of mg/liters/hour or in mg/liter as a final titer after six days. (8,8a-deoxyoleandolide is the same as 6-dEB except that it contains methyl instead of ethyl as position 12, since acetyl CoA rather than propionyl CoA is used as a starter unit.) More specifically, after six days CH999/pFL494 plus methylmalonic acid produced 180 mg/l 6-dEB and about 90 mg/l of 8,8a-deoxyoleandolide. If methylmalonic acid was not added to the medium, 6-dEB was produced at a level of 130 mg/l while 8,8a-deoxyoleandolide was produced at bout 40 mg/l. For CH999 modified to contain pCK7, in the presence of methylmalonic acid in the medium, only 60 mg/l 6-dEB were formed along with about 20 mg/l of 8,8a-deoxyoleandolide. Without methylmalonic acid, these cells produced slightly less of each of these macrolides.

3. CH999/pFL494 completely consumed methylmalonate supplied at 1 g/L by day 6.

4. Consumption of 1 g/L methylmalonate results in a cumulative increase in macrolide of 200 m/L, representing a 35% conversion efficiency of methylmalonate into products.

5. CH999/pFL494 shows improved production of both macrolides even in the absence of exogenous methylmalonate (see 2 above).

6. Even CH999/pCK7 showed a 20% improvement in 6-dEB production when exogenous methylmalonate was added (see 2 above).

In addition to enhancing the productivity of known polyketides in natural and heterologous hosts, MatB is also used to produce novel polyketides. In contrast to other enzymes that produce the alpha-carboxylated CoA thioester building blocks for polyketide biosynthesis, such as methylmalonyl-CoA mutase (which has a high degree of specificity for succinyl-CoA) and acetyl/propionyl-CoA carboxylase (which prefers acetyl-CoA and/or propionyl-CoA), MatB is active with respect to a wide range of substrates. In addition to malonate and methylmalonate, MatB is able to activate substrates such as ethylmalonate, dimethylmalonate, isopropylmalonate, propylmalonate, allylmalonate, cyclopropylmalonate, and cyclobutylmalonate into their corresponding CoA thioesters.

Incorporation of these substrates into polyketide synthases requires a suitable acyltransferase (AT) which may be engineered into the appropriate module of a polyketide synthase, so that it can accept the unnatural substrate. Though none of these dicarboxylic acids yield detectable quantities of novel compounds when fed to CH999/pFL494, certain PKS enzymes naturally possess AT domains with orthogonal substrate specificity. For example, the FK506 PKS contains an acyltransferase domain that ordinarily incorporates bulky substrates such as propylmalonyl-CoA in preference to substrates such as malonyl-CoA or methylmalonyl-CoA, and can thus accept MatB-generated unnatural building blocks without any PKS engineering.

Using a protein engineering strategy described by Lau, J., et al., *Biochemistry* (1999) 38:1643–1651, the AT domain of module 6 of DEBS in pFL494 was modified to include the specificity determining segment from the niddamycin AT4 domain which incorporates ethylmalonyl-CoA. See: Kakavas, S. J., et al., *J Bacteriol* (1997) 179:7515–7522. The resulting plasmid pFL508 was transformed into CH999. Upon feeding this strain with ethylmalonate, mass spectroscopy was able to detect a product corresponding to 2-ethyl-6dEB in levels comparable to that of 6dEB. The new compound was undetectable in the absence of ethylmalonate or in a control strain lacking the matBC genes.

EXAMPLE 4

Production of 6-dEB in *E. coli*

We have demonstrated the ability of *E. coli* to produce complex, complete, polyketides, when programmed with the ability to express a functional PKS, a pantetheinyltransferase, and one or more pathways for producing starter and extender units. *E. coli* strain BL-21 (DE) obtained from Novagen was modified genetically by inserting the phosphopantetheinyl transferase gene (the sfp gene) from *Bacillus subtilis* into the chromosome under the control of the phage T7 promoter by deleting the prpA-D portion of the prp operon, thus also placing the prpE locus, which encodes a propionyl CoA synthetase, under control of the T7 promoter. This genetically modified strain was then modified to include expression systems for the three genes encoding the DEBS 1, DEBS2, and DEBS3 proteins, also under control of the T7 promoter as well as genes encoding propionyl CoA carboxylase and a gene encoding biotin ligase which is necessary for activation of the propionyl CoA carboxylase enzyme. The resulting *E. coli* contains a complete synthase for 6-dEB, a phosphopantetheinyl transferase necessary for the activation of this PKS, the propionyl CoA carboxylase enzymes that supply methylmalonyl CoA from propionyl CoA, and an inducible means to produce the endogenous propionyl CoA synthase capable of converting exogenous propionate to propionyl CoA. In addition, the endogenous system for catabolism of propionate was disarmed.

Thus, the *E. coli* are provided enzymes for synthesis of both starter and extender units under control of an inducible promoter, the endogenous mechanism for destruction of the propionate precursor of the starter and extender units has been disarmed; and expression systems (also under inducible promoters) have been provided for the necessary PKS proteins along with an expression system for the enzyme for activation of the PKS proteins.

In more detail, the genetically modified BL-21(DE3) strain was prepared according to the procedure described in Hamilton, et al., *J Bacteriol* (1989) 171:4617–4622. A derivative of pMAK705 described in this publication, was prepared. In the derived vector, a T7 promoter coupled to the sfp gene was flanked by a 1,000 base pair sequence identical to that upstream of the A locus of the prp operon and a 1,000 base pair sequence identical to the sequence downstream of the E locus of this operon. The sfp gene was obtained from pUC8-sfp, a plasmid described by Nakano, et al., *Mol. Gen. Genet.* (1992) 232:313–321. The resulting integrated sequence deletes the prp loci A-D and inserts the T7 promoter controlling the sfp gene in their place and further results in placing the prpE locus under the control of the T7 promoter. The T7 promoter is inducible by IPTG.

The resulting genetically altered host, designated BAP 1, was than transfected with three plasmids each selectable for a different antibiotic resistance. These plasmids are as follows:

pBP 130 is derived from pET21 (carb$^R$) obtained from Novagen and modified to contain the DEBS2 and DEBS3 genes under control of the T7 promoter.

pBP144 is a modified form of pET28 (kan$^R$) also available from Novagen containing the pcc and DEBS1 genes, also under control of the T7 promoter.

pCY214 (cm$^R$) contains the *E. coli* birA (biotin ligase) gene under the ara promoter and is described in Chapman-Smith, et al., *Biochem. J.* (1994) 302:881–887. The PCC protein and pcc gene are described in Rodriguez, et al., *Microbiol.* (1999) 145:3109–3119.

For the production of 6-dEB, BAP1 cells transformed with pBP130, pBP144, and pCY214 were grown in M9 minimal media with the appropriate antibiotics. The culture was grown to mid-log phase, followed by induction with IPTG and arabinose and the concomitant addition of 250 mg/L $^{13}$C-1-propionate. Induced cultures were grown for 12–24 hrs at 22° C. (Both the minimal medium and lower temperatures were found to be beneficial for DEBS gene expression. This protocol permitted growth-related production of 6-dEB, since glucose provided the carbon and energy source for general metabolism, while propionate was converted into 6-dEB.)

After 12–24 h the culture supernatant was extracted with ethyl acetate. The organic phase was dried in vacuo, and re-dissolved in CDCl$_3$ for $^{13}$C-NMR analysis. The accompanying spectrum showed that 6-dEB was the major $^{13}$C-labeled product. Other major $^{13}$C-labeled compound(s) with peaks in the range of 120–140 ppm are not derived from propionate incorporation, as confirmed by a separate experiment in which $^{13}$C-3-propionate was used in lieu of $^3$C-1-propionate. From the intensities of peaks corresponding to 6-dEB, it is estimated that at least 75% of the exogenous propionate was converted into 6-dEB. This was consistent with the disappearance of the propionate signal from the $^{13}$C NMR spectrum of the culture medium at the end of the fermentation. Negative control strains, which lacked either pBP130 or pBP144, failed to yield detectable quantities of 6-dEB.

The foregoing experiments were performed at low cell densities ($OD_{600}$ in the range of 0.5–2.5); a major advantage of synthesizing recombinant products in E. coli is that this bacterium can be grown to extremely high cell densities ($OD_{600}$ of 100–200) without significant loss in its specific catalytic activity.

The use of the matB and C genes or any of their homologs from other organisms in a non-native expression system is useful as a general strategy for the in vivo production of any alpha-carboxylated CoA thioester in any microbial host. The in vivo production of such CoA thioesters could be intended to enhance natural polyketide productivity or to produce novel polyketides. The matA gene is also useful to supplement in vivo levels of substrates such as acetyl-CoA and propionyl-CoA. Purified MatB is also used for the preparative in vitro production of polyketides, since CoA thioesters are the most expensive components in such cell-free synthesis systems.

EXAMPLE 5

Incorporation of Diketides

The BAP1 E. Coli host organism described in Example 4 was transfected with p132 which contains an expression system for the PCCA and B subunits and with pRSG36 which contains an expression system for module 6+TE of DEBS3. The transfected cultures were grown on minimal selection media for both plasmids and then fed $^{14}$C labeled diketide. When induced and provided with propionate, $^{14}$C labeled triketide was obtained.

What is claimed is:

1. A recombinant Streptomyces host cell which is genetically modified for enhanced synthesis of a polyketide, wherein said modification comprises incorporation of the matBC gene from Streptomyces coelicolor or the matBC gene from Rhizobium trifoli wherein the matBC gene is in addition to endogenous matBC.

2. The host cell as in claim 1 wherein the modification further comprises incorporation of the matA gene from Rhizobium trifoli.

3. The host cell as in claim 1 wherein said modification further comprises incorporation of at least one expression system for a modular polyketide synthase (PKS).

4. The host cell as in claim 3 wherein the PKS is DEBS.

5. The host cell as in claim 1 wherein the host cell is Streptomyces coelicolor.

6. The host cell as in claim 1 wherein the matBC gene is from Rhizobium trifoli.

7. The host cell as in claim 1 wherein the polyketide is 6-dEB.

8. A method to produce a polyketide which method comprises culturing the cells of claim 1 under conditions wherein said polyketide is produced.

9. The method of claim 8 which further includes providing a substrate, wherein the substrate is of the formula $RCH(COOH)_2$ wherein R is H, methyl or ethyl.

10. A method to assess polyketide production in a host cell containing shuffled polyketide synthase (PKS) genes, said method comprising:
a) shuffling PKS genes or functional domains thereof to produce a mixture of rearranged PKS genes,
b) transforming a culture of Streptomyces according to claim 1 with said mixture,
c) culturing individual colonies of said transformed Streptomyces, and
d) assessing each colony for polyketide production,
wherein colonies, which produce polyketides, contain successfully shuffled genes.

11. The methods of claim 10, wherein said host cell is Streptomyces coelicolor.

12. A method to assess polyketide production in a host cell containing mutated polyketide synthase (PKS) genes, said method comprising:
a) mutating PKS genes to produce a mixture of mutated PKS genes,
b) transforming a culture of Streptomyces according to claim 1 with said mixture,
c) culturing individual colonies of said transformed Streptomyces, and
d) assessing each colony for polyketide production,
wherein colonies, which produce polyketides, contain successfully mutated genes.

13. The method of claim 12, wherein said host cell is Streptomyces coelicolor.

14. A recombinant E. coli host cell which is genetically modified for synthesis of a polyketide, wherein said modification comprises:
a) incorporation of the matBC gene from Streptomyces coelicolor or the matBC gene from Rhizobium trifoli,
b) incorporation of at least one expression system for a modular polyketide synthase, and
c) incorporation of the sfp gene from Bacillus subtilis.

15. The host cell as in claim 14 wherein the modification further comprises incorporation of the matA gene from Rhizobium trifoli.

16. The host cell as in claim 14 wherein the matBC gene is from Rhizobium trifoli.

17. The host cell as in claim 14 wherein the PKS is DEBS.

18. The host cell as in claim 14 wherein the polyketide is 6-dEB.

19. A method to produce a polyketide which method comprises culturing the cells of claim 14 under conditions wherein said polyketide is produced.

20. The method of claim 19 which further includes providing a substrate, wherein the substrate is of the formula $RCH(COOH)_2$ wherein R is H, methyl or ethyl.

21. A method to assess polyketide production in a host cell containing shuffled polyketide synthase (PKS) genes, said method comprising:
a) shuffling PKS genes or functional domains thereof to produce a mixture of rearranged PKS genes,
b) transforming a culture of E. coli according to claim 14 with said mixture,
c) culturing individual colonies of said transformed E. coli, and
d) assessing each colony for polyketide production,
wherein colonies, which produce polyketides, contain successfully shuffled genes.

22. A method to assess polyketide production in a host cell containing mutated polyketide synthase (PKS) genes, said method comprising:
   a) mutating PKS genes to produce a mixture of mutated PKS genes,
   b) transforming a culture of *E. coli* according to claim 14 with said mixture,
   c) culturing individual colonies of said transformed *E. coli*, and
   d) assessing each colony for polyketide production, wherein colonies, which produce polyketides, contain successfully mutated genes.

23. A recombinant *E. coli* host cell which is genetically modified for synthesis of a polyketide, wherein said modification comprises
   a) incorporation of a propionyl CoA carboxylase (pcc) expression system comprising the pccB and accA2 genes from *Streptomyces coelicolor* wherein said pcc expression system produces an enzyme capable of synthesizing 2S-methylmalonyl CoA,
   b) incorporation of at least one expression system for a modular polyketide synthase, and
   c) incorporation of the sfp gene from *Bacillus subtilis*, wherein the cell's prpA-D operon is deleted.

24. A method to produce a polyketide which method comprises culturing the cells of claim 23 under conditions wherein said polyketide is produced.

25. The method of claim 24, which further includes providing a substrate, wherein the substrate is of the formula $RCH(COOH)_2$ wherein R is H, methyl or ethyl.

26. A method to assess polyketide production in a host cell containing shuffled polyketide synthase (PKS) genes, said method comprising:
   a) shuffling PKS genes or functional domains thereof to produce a mixture of rearranged PKS genes,
   b) transforming a culture of *E. coli* according to claim 23 with said mixture,
   c) culturing individual colonies of said transformed *E. coli*, and
   d) assessing each colony for polyketide production, wherein colonies, which produce polyketides, contain successfully shuffled genes.

27. A method to assess polyketide production in a host cell containing mutated polyketide synthase (PKS) genes, said method comprising:
   a) mutating PKS genes to produce a mixture of mutated PKS genes,
   b) transforming a culture of *E. coli* according to claim 23 with said mixture,
   c) culturing individual colonies of said transformed *E. coli*, and
   d) assessing each colony for polyketide production, wherein colonies, which produce polyketides, contain successfully mutated genes.

* * * * *